United States Patent [19]

Jalkanen et al.

[11] Patent Number: 5,422,243

[45] Date of Patent: Jun. 6, 1995

[54] DETECTION OF SYNDECAN CONTENT IN BIOLOGICAL MATERIALS SUCH AS TISSUES AND BODY FLUIDS FOR INDICATIONS OF MALIGNANT TRANSFORMATIONS OF CELLS

[76] Inventors: Markku T. Jalkanen, 061254-1178 Rauvolantie, 20760 Piispanristi; Rirjo L. K. Inki, 100765-060T, Talikkokatu 8 D 59, 20540 Turku; Jarkko Kirjavainen, 050266-077B, Sirkkalankatu 4 C 50, 20520 Turku; Sirpa M. Leppä, 040766-078S, Kulmalankatu 4, 20540 Turku; Sakari M. Mali, 120966-135c, Yo-kylä 6 D 6, 20510 Turku, all of Finland

[21] Appl. No.: 144,547

[22] Filed: Nov. 1, 1993

Related U.S. Application Data

[63] Continuation of Ser. No. 721,330, Jul. 1, 1991, abandoned, which is a continuation-in-part of Ser. No. 641,209, Jan. 15, 1991, abandoned.

[51] Int. Cl.$^6$ .................... C12Q 1/00; G01N 33/53; G02F 1/01
[52] U.S. Cl. ........................ 435/6; 435/7.21; 435/7.8; 435/7.23; 435/7.1; 530/353
[58] Field of Search ............... 435/7.8, 7.23, 7.1, 435/7.21, 6, 7.4; 530/350, 353

[56] References Cited

U.S. PATENT DOCUMENTS 4,859,581 8/1989 Nicolson et al. .................... 435/4

FOREIGN PATENT DOCUMENTS

WO90/12033 10/1990 WIPO .
WO93/05167 3/1993 WIPO .

OTHER PUBLICATIONS

Mali et al., *J. Biol. Chem.* 265(12):6884–6889, Apr. 25, 1990.
Elenius et al., *J. Biol. Chem.* 265(29):17837–17843, Oct. 15, 1990.
Jalkanen et al., *J. Cell Biol.*, 105(6):3087–3096, Dec. 1987.
Buck, C. A. et al., Integrin, a Transmembrane Glycoprotein Complex Mediating Cell–Substratum Adhesion, *J. Cell Sci. Suppl.* 8:231–250 (1987).
Elenius, K. et al., Induced Expression of Syndecan in Healing Wounds, *J. Cell Biol.* 114(3):585–595 (1991).
Hayashi, K. et al., Immunocytochemistry of Cell Surface Heparan Sulfate Proteoglycan in Mouse Tissues. A Light and Electron Microscopic Study, *J. Histochem. Cytochem.* 35(10):1079–1088 (1987).
Inki, P. et al., Immunohistochemical Localization of Syndecan in Mouse Skin Tumors Induced by UV Irradiation, *Am. J. Path.* 139(6):1333–1340 (1991).
Jalkanen, M., Biology of Cell Surface Heparan Sufate Proteoglycans, *Med. Biol.* 65:41–47 (1987).
Jalkanen, M. et al., Syndecan, a Regulator of Cell Behavior, is Lost in Malignant Transformation, *Chem. Abstrs.* 115(17):655, Abstract No. 180472e (1991).
Jalkanen, M. et al., Syndecan, a Regulator of Cell Behaviour, is Lost in Malignant Transformation, *Biochem. Soc. Trans.* 19:1069–1072 (1991).
Jalkanen, M. et al., Simultaneus Loss of Syndecan Expression and Epithelial Phenotype in S115 Carcinoma Cells Exposed to Steroids, *J. Cell. Biochem. Suppl. 0 (14 Part A)*:153 Abstract No. A113 (1990).
Jalkanen, M. et al., Syndecan Expression is Suppressed (List continued on next page.)

*Primary Examiner*—Robert A. Wax
*Assistant Examiner*—Keith D. Hendricks
*Attorney, Agent, or Firm*—Sterne, Kessler, Goldstein & Fox

[57] ABSTRACT

A method for detecting a potentially detrimental transformation of cells of an organism. The method comprises determining syndecan content indicator from a sample of biological material from the organism, and comparing the determined syndecan content indicator with a reference syndecan content indicator from a reference biological material of the same type.

16 Claims, 4 Drawing Sheets

OTHER PUBLICATIONS in Steroid–Induced Transformation of Mouse Mammary Tumor Cell Line, *J. Cell Biol.* 109:320a, Abstract No. 1758 (1989).

Jalkanen, M. et al., Binding of Extracellular Effector Molecules by Cell Surface Proteoglycans, *Receptors for Extracellular Matrix:*1–37 (1991).

Jalkanen, M. et al., Loss of Syndecan Expression in Mouse Mammary Epithelial Cells After Transformation with a Point-Mutated c–Ha-*ras* Proto-Oncogene, *J. Cell. Biochem. Suppl.* 0 (*13 Part B*):52 Abstract No. D317 (1989).

Jalkanen, M. et al., Heparan Sulfate Proteoglycans from Mouse Mammary Epithelial Cells: Localization on the Cell Surface with a Monoclonal Antibody, *J. Cell Biol.* 101:976–984 (1985).

Koda, J. E. et al., Heparan Sulfate Proteoglycans from Mouse Mammary Epithelial Cells, *J. Biol. Chem.* 260(13):8157–8162 (1985).

Leppä, S. et al., Steroid–Induced Epithelial-Fibroblastic Conversion Associated with Syndecan Suppression in S115 Mouse Mammary Tumor Cells, *Cell Reg.* 2:1–11 (1991).

Rapraeger, A. et al., Cell Surface Proteoglycan Associates with the Cytoskeleton at the Basolateral Cell Surface of Mouse Mammary Epithelial Cells, *J. Cell Biol.* 103 (*No. 6, Pt. 2*):2683–2696 (1986).

Rapraeger, A. et al., The Cell Surface Proteoglycan from Mouse Mammary Epithelial Cells Bears Chondroitin Sulfate and Heparan Sufate Glycosaminoglycans, *J. Biol. Chem.* 260(20):11046–11052 (1985).

Sanderson, R. D. et al., Molecular Polymorphism of a Cell Surface Proteoglycan: Distinct Structures on Simple and Stratified Epithelia, *Proc. Natl. Acad. Sci. USA* 85:9562–9566 (1988).

Saunders, S. et al., Cell Surface Proteoglycan Binds Mouse Mammary Epithelial Cells to Fibronectin and Behaves as a Receptor for Interstitial Matrix, *J. Cell Biol.* 106:423–430 (1988).

Saunders, S. et al., Molecular Cloning of Syndecan, an Integral Membrane Proteoglycan, *J. Cell Biol.* 108:1547–1556 (1989).

Saunders, S. et al., Mammary Epithelial Cells Transfected with Antisense cDNA Reduce Cell Surface Syndecan and Become Fibroblastic in Morphology, *J. Cell. Biol.* 109:5(a), Abstract No. 7 (1989).

Thesleff, I. et al., Cell Surface Proteoglycan Expression Correlates with Epithelial-Mesenchymal Interation During Tooth Morphogenesis, *Devel. Biol.* 129:565–572 (1988).

Vainio, S. et al., Syndecan and Tenascin Expression is Induced by Epithelial-Mesenchymal Interactions in Embryonic Tooth Mesenchyme, *J. Cell Biol.* 108:1945–1954 (1989).

Vainio, S. et al., Epithelial-Mesenchymal Interactions Regulate the Stage-Specific Expression of a Cell Surface Proteoglycan, Syndecan, in the Developing Kidney, *Devel. Biol.* 134:382–391 (1989).

DETECTION OF SYNDECAN CONTENT IN BIOLOGICAL MATERIALS SUCH AS TISSUES AND BODY FLUIDS FOR INDICATIONS OF MALIGNANT TRANSFORMATIONS OF CELLS

This application is a continuation of application Ser. No. 07/721,330, filed Jul. 1, 1991, now abandoned, which is a continuation-in-part application of Ser. No. 641,209, filed Jan. 15, 1991, now abandoned.

The present invention relates generally to the field of biology such as cancer biology, and more specifically relates to methods for detecting premalignant or malignant tissues by, in one aspect, the detection of syndecan loss in tissues and by, in another aspect, the detection of the appearance of syndecan in human body fluids, with procedures which may utilize syndecan specific liquids, antibodies and cDNA probes for the detection.

Cell surface molecules, which function in specific interactions between the cell surface and the extracellular matrix (ECM), are called matrix receptors. The recognition of matrix by these receptors plays an important role in the regulation of cell shape, profileration and differentiation, and is therefore a critical event in the normal development of organs and maintenance of tissue architecture. Known matrix receptors include, for example, a family of transmembrane glycoprotein receptors that share common structural and functional characteristics and are called integrins (Hynes, R. (1987) *Cell* 48: 549–554), a 67-kDa glycoprotein, which binds to laminin B1-chain (Graf et al (1987) *Cell* 48: 989–996) and cell surface proteoglycans (PG) which, depending on glycosaminoglycan composition (e.g., heparan sulfate), can interact with a variety of matrix molecules (Jalkanen, M. (1987) *Med. Biol.* 65: 41–47).

Cell adhesion, spreading, proliferation and differentiation are all based on close contacts between the cell surface and the surrounding extracellular matrix (ECM). The selective usage of ligand-receptor interaction may in vivo create the diversity of specific cell-matrix interactions needed for the development of organs (Ekblom et al. (1986) *Ann. Rev. Cell Biol.* 2:27–47). Transformation is known to alter the response of cells to ECM (Liotta, L. (1986) *Cancer Res.* 46:1–7), suggesting that changes in the expression of matrix receptors by malignant cells can occur (Plantefaber and Hynes (1989) *Cell* 56;281–290; Cheresh et al. (1989) *Cell* 57: 59–69). These changes are largely unknown, but may have a fundamental role in the outcome of malignant behavior of various cell types.

The cell surface proteoglycan of mouse mammary epithelial cells consists of a lipophilic membrane domain (Rapraeger and Bernfield (1983) *J. Biol. Chem.* 258:3632–3636; (1985) *J. Biol. Chem.* 260:4103–4109) and of a matrix interacting ectodomain containing both heparan sulfate and chondroitin sulfate chains (Rapraeger et al(1985) *J. Biol. Chem.* 260: 11046–11052). Recent cDNA-cloning of mouse and human syndecans has confirmed these functional domains on the core protein and this PG has been named syndecan (Saunders et al. (1989) *J. Cell Biol.* 108:1547–1556; Mali et al. (1990) *J. Biol. Chem.* 265:6884–6889). The ectodomain of syndecan is recognized by mAb 281-2 (Jalkanen et al. (1985) *J. Cell Biol.* 101:976–984; Jalkanen et al. (1987) *J. Cell Biol.* 105:3087–3096) and it binds with high affinity to Type I, III and V collagen fibrils (Koda et al. (1985)*J. Biol. Chem.* 260:8157–8162) and with lower affinity to C-terminal heparin binding domain of fibronectin (Saunders and Bernfield (1988) *J. Cell Biol.* 106:423–430), thrombospondin (Sun et al. (1989) *J. Biol. Chem.* 264:2885–2889) and tenascin (Salmivirta et al. (1991) *J. Biol. Chem.* 266: in press). The ligand binding promotes the association of the membrane domain to actin-rich cytoskeleton (Rapraeger et al. (1986) *J. Cell Biol.* 103:2683–2696). The epithelial cells, however, can also shed the ectodomain from the cell surface by a proteolytic cleavage of the core protein that separates the ectodomain from the membrane domain (Jalkanen et al. (1987) *J. Cell Biol.* 105:3087–3096; Weitzhandler et al. (1988) *J. Biol. Chem.* 263:6949–6952). Therefore syndecan can link the epithelial cytoskeleton to the matrix but also loosen epithelial association with the matrix. By these associations, syndecan can mediate matrix organization into cellular organization and influence the behavior of cells. Because syndecan mainly interacts with stromal components like collagen fibrils and fibronectin, syndecan may function as a communicator between epithelial and mesenchymal tissues. This type of communication is critical for normal epithelial differentiation and organ formation.

The expression of syndecan during development and organ formation follows morphogenetic rather than histological boundaries (Thesleff et al. (1988) *Dev. Biol.* 189:565–572), a feature which also supports an active role for syndecan as a matrix receptor during development. Syndecan has been localized mainly on various epithelial cells (Hayashi et al. (1987) *J. Histochem. Cytochem.* 35:1079–1088) but can also be found on the surfaces of plasma cells (Sanderson and Bernfield (1988) *Proc. Natl. Acad. Sci. USA* 85:9562–9566). Syndecan localizes also to condensating mesenchyme next to budding epithelium during organ formation (Thesleff et al. (1988) *Dev. Biol.* 189: 565–572). Its expression in the mesenchyme has been shown to be regulated by epithelial contact both in tooth (Vainio et al. (1988) and in metanephric kidney (Vainio et al. (1989), and in both tissues, its expression can be correlated both spatially and temporally to the morphogenesis of these organs.

SUMMARY OF THE INVENTION

It is therefore an object of the subject invention to provide a method for the detection of premalignant or malignant tissues by detection of syndecan loss from the tissues.

It is another object of the present invention to provide a method for the detection of premalignant or malignant tissues by the detection of the appearance of syndecan in body fluids.

It is a further object of the present invention to provide a method which is particularly adaptable for the detection of malignant or premalignant tissues in humans.

It is yet another object of the present invention to provide a biochemical, immunohistological or molecular biological method to detect syndecan expression or syndecan content in tissues or body fluids in order to detect malignant or premalignant transformations of cells.

It is a further object of the present invention to provide a method for detecting hyperplastic changes in cells.

It is an additional object of the present invention to provide a method for detecting proposed hyperplastic changes in cells.

It is yet another object of the present invention to provide a method for detecting proposed morphological changes in cells.

It is also an object of the present invention to provide a method for the quantitation of syndecan in tissues or body fluids to produce an indicator value.

Briefly, in its broader aspects the present invention comprehends a method for detecting a potentially detrimental transformation of cells of an organism, the method comprising determining a syndecan content indicator from a sample of biological material from the organism, and comparing the determined syndecan content indicator with a reference syndecan content indicator from a reference biological material, preferably a material of the same type.

The subject method may be accomplished in a variety of manners including biochemical, immunohistological or molecular biological type methods. While the method is applicable to detecting a detrimental transformation such as a malignant or premalignant condition in a wide variety of organisms, it is particularly adaptable for detecting a detrimental transformation in cells, particularly in human cells. Transformations which may be detected include premalignant and malignant transformations including hyperplastic and morphological changes.

Detection of the presence or lack thereof of syndecan may be conducted on various biological materials of the organism such as cells, tissues and body fluids including, particularly for human biological materials, serum, plasma, urine, spinal fluid or other tissue extracts. Detection of syndecan content in biological materials can be accomplished by the use a variety of means including syndecan specific ligands or biochemical determinants, syndecan specific antibodies, and syndecan antisense mRNAs or cDNAs or oligonucleotides.

Further features, objects and advantages of the present invention will become more fully apparent from a detailed consideration of the following description of the subject invention when taken together with the accompanying drawings.

DETAILED DESCRIPTION OF THE PREFERRED EMBODIMENTS

The present invention is based, in part, on findings that syndecan detection is a valuable diagnostic criteria for the estimation of the malignancy in biological materials such as epithelial cells. Examples are given for three different kinds of experimental manners to induce transformation (hormonal induction, UV-irradiation and oncogene induction), and in each of them, syndecan loss was shown to be evident. Detection of syndecan loss is valuable also in other mechanisms leading to a transformation such as tumor formation, and therefore the present invention is not restricted only to those mentioned above. For example, syndecan detection can provide valuable information also in several proliferative stages of tissues (e.g. of skin, kidney, brain, lung, bladder), which later may turn into more malignant stage. These so-called premalignant stages, which are often seen as dysplasias, express variable levels of syndecan, which is information needed to estimate the seriousness of the disease so as to provide appropriate therapeutic treatment. An important area of syndecan detection is also in circulating plasma cells. Therefore their analysis by the subject method, which utilizes syndecan specific antibodies, such as FACS-analysis (fluorescent activated cell sorter), provides valuable information for the pathophysiological condition of a patient with lymphoma, myeloma, leukemia or other proliferative stage of hematopoietic cells.

Syndecan is also known to be shed from the cell surface (Jalkanen et al. (1987) J. Cell Biol. 105:3087–3096), and it could be that in certain diseases, the loss of syndecan from cell surfaces may result in the appearance of it in the body fluids. Therefore, in accordance with the present invention, it is of diagnostic value to measure syndecan amounts in serum, plasma, urine, spinal fluid or other tissue extracts, in order to determine how much tissue destruction and disappearance of normal cell morphology has taken place in the studied tissues.

As previously mentioned, syndecan is a cell surface proteoglycan consisting of covalently linked glycosaminoglycan (GAG) chains and a membrane embedded core protein (Saunders et al. (1989) J. Cell. Biol. 108, 1547–1556). GAG-chains of syndecan are known to belong to groups of heparan sulfate and chondroitin sulfate (Rapraeger et al. (1985) J. Biol. Chem. 260:11046–11052), and they are not limited to syndecan. The core protein of syndecan is unique and defines this molecule as a member of several similar cell surface proteoglycans (Mali et al. (1990) J. Biol. Chem. 265:6884–6889). Murine syndecan was originally isolated and still commonly detected with a monoclonal antibody (MnAb 281-2) against the core protein of syndecan (Jalkanen et al. (1985) J. Cell Biol. 101:976–984).

To further explain the present invention, syndecan expression was analyzed in relation to the induction of malignant phenotype in three different independent biological models, each of them resulting in the malignant transformation of epithelial cells. In all of these models, the loss of syndecan expression was observed simultaneously with malignant transformation. These results are briefly presented in the following models for illustration of the subject invention.

In the first model, a Shionogi 115 (S115) mouse mammary tumor cell line was used. Such cells provide an excellent model for studies of the transformed phenotype because they respond to androgens by increasing growth rate (King et al. (1976) J. Steroid Biochem. 7:869–873) and by changing from epithelial to fibroblastic morphology (Yates and King (1981) Cancer Res.

41:258–262). In the presence of an androgen, the cells adhere loosely to substratum and acquire an ability to grow in suspension without anchorage to matrix, whereas in the absence of androgen they adhere tightly to the matrix and do not grow at all in suspension (Yates and King (1981) Cancer Res. 41:258–262). The basis for the morphological change and for anchorage independency is largely unknown although several mechanisms, including changes in cytoskeletal organization (Couchman et al. (1981) Cancer Res. 41:263–269) and in paracrine mechanisms (Darbre and King (1988) In Breast Cancer: Cellular and Molecular Biology, ed. M. E. Lippman and R. B. Dickson, Academic Publishers, pp 307–341), have been proposed.

Testosterone-treated S115 cells revealed strong RGDS-dependent binding to fibronectin (FN), but no binding to the heparin-binding domain of FN, thus indicating that they expressed integrin-like molecules. Instead, S115 cells grown without testosterone showed epithelial morphology and binding to the heparin-binding domain of FN, indicating an alteration of syndecan expression in hormone treated S115 cells. Both the amounts of matrix-binding ectodomain of syndecan, when quantitated by radio-immunoassay and by Western-blot, and of syndecan mRNA (2.6 kb) declined in hormone-treated S115 cells. The addition of antiandrogen cyproterone acetate to culture medium opposed the effect of testosterone on syndecan mRNA. Thus, the inactivation of syndecan gene and the consequent suppression of syndecan expression is related to the altered adhesion properties, disappearance of epithelial phenotype and, on the other hand, to the appearance of transformed-like phenotype in hormone-treated S115 cells.

Figure 1A:
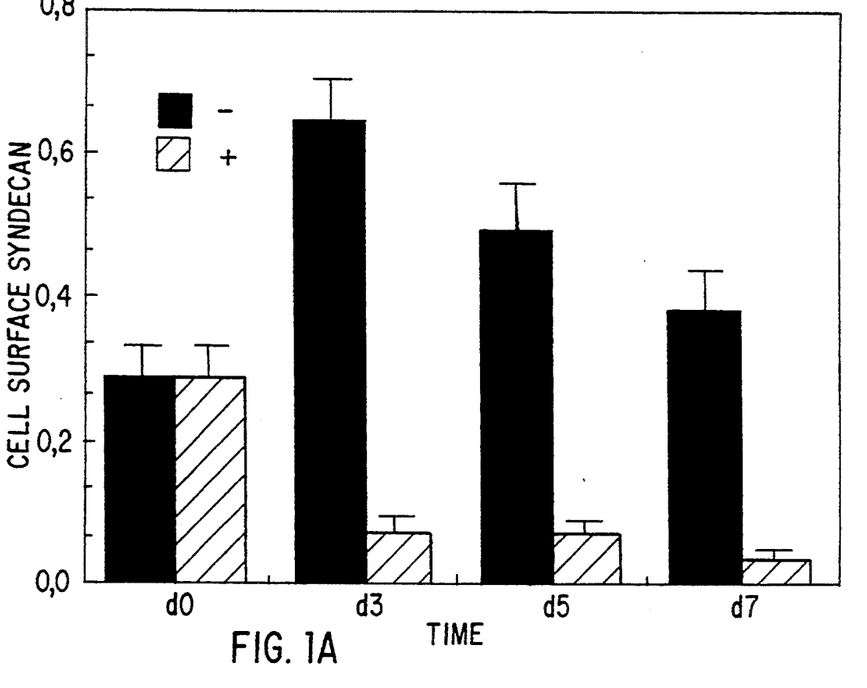
FIG. 1A is a graphical representation of cell surface syndecan content versus time illustrating syndecan loss in mouse mammary epithelial cells transformed by exposure to testosterone.
Figure 1B:
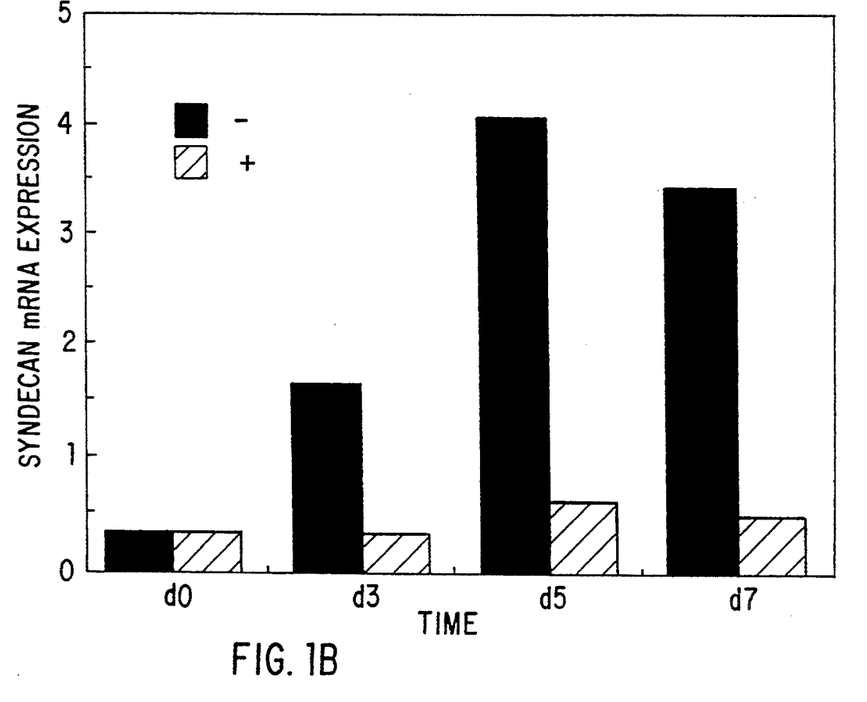
FIG. 1B is a graphical representation of syndecan mRNA expression versus time illustrating syndecan loss in mouse mammary epithelial cells transformed by exposure to testosterone.

An example of the above results is presented in FIGS. 1A and 1B. FIG. 1A is a comparative graphical representation of cell surface syndecan content versus time illustrating syndecan loss in mouse mammary epithelial cells (S115) transformed by exposure to testosterone and FIG. 1B is a comparative graphical representation of syndecan mRNA expression versus time illustrating syndecan loss in mouse mammary epithelial cells transformed by exposure to testosterone. These representations show malignant behavior and loss of syndecan expression that is evident in the protein of FIG. 1A and mRNA level of FIG. 1B after the exposure.

From the above, the addition of androgen to S115 cultures results in the suppression of syndecan expression due to the inactivation of syndecan gene. This suppression closely correlates to the acquisition of anchorage independency and to the loss of epithelial phenotype, and thus is one of the reasons for the outcome of transformed-like behavior of S115 cells in the presence of androgen.

In the second model, immunoreactivity for syndecan was studied in hairless (hr/hr) mice exposed to UV-A and UV-B irradiation. Positive staining was observed at the surface of normal epidermal cells as well as in the dermal abortive hair follicle cysts characteristic to this mouse strain. Early reaction to UV-irradiation showing hyperplastic epidermis with slight cellular atypia was also positive, although reduced staining of epidermal cell surfaces. Specimens with severe dysplasia showed weak staining in the granular cell layer, whereas the basal cell layer was negative. In papillomas and in the sole keratoacanthoma, immunoreactivity for syndecan was observed in the benign hyperplastic epidermal cells as well as in the proliferating epidermal cells of the horn cysts. Malignant transformation expressed as the formation of squamous cell carcinomas and sarcomas was uniformly associated with loss of syndecan staining. These results are consistent with the previous findings of reduced expression of syndecan associated with malignant transformation of cultured epithelial cells, but also suggest an important role for syndecan in the maintenance of normal tissue architecture and differentiation pattern of the skin.

Figure 2A:
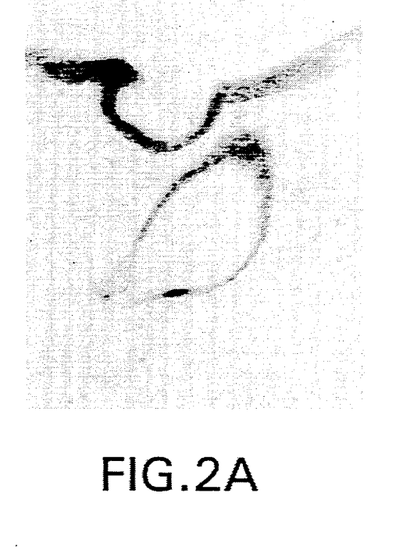
FIGS. 2A through 2D are illustrations of photographs of sections of mouse biological skin material showing the progression of syndecan expression after exposure of the material to UV light.
Figure 2B:
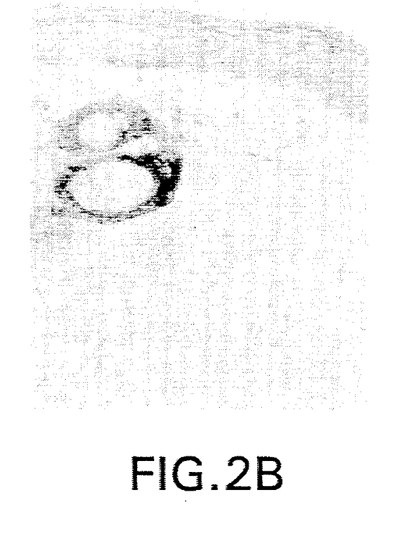
Figure 2C:
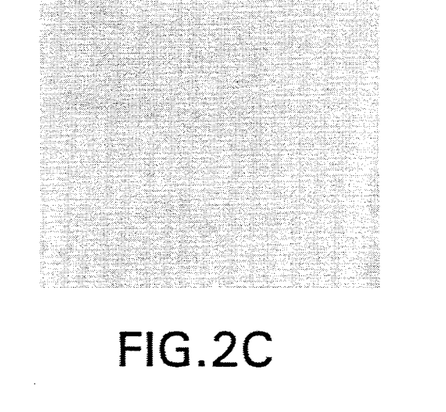
Figure 2D:
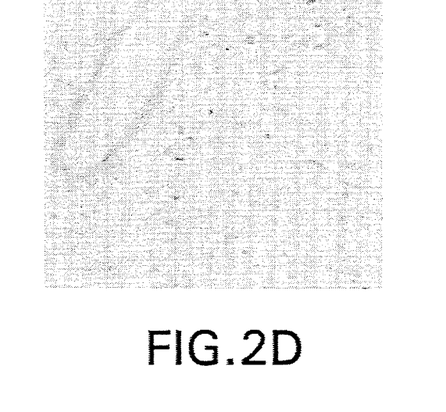

Examples of these stainings are shown in FIGS. 2A through 2D. These figures are illustrations of photographs of sections of mouse biological skin material showing the progression of syndecan expression after exposure of the material to UV light. FIG. 2A shows normal skin material and FIGS. 2B and 2C illustrate different stages of hyperplasia, the section shown in FIG. 2C indicating some malignant histology. These figures show premalignant hyperplasia induced by UV irradiation gradually lose syndecan expression.

From the above, it is apparent that epithelial cells in vivo and embedded to their normal environment lose syndecan expression during the process of malignant transformation, indicating again that syndecan expression is needed for the normal cell morphology and tissue integrity, but also that the loss of syndecan expression can be correlated to the seriousness of dysplasia and malignancy of epithelial cells.

In the third model, a point mutated c-Ha-ras gene transfected mouse mammary epithelial cell line was used. A c-Ha-ras gene is under MMTV-LTR promoter in these NOG-8 ras cells and thus its expression can be regulated by dexamethasone (Ciardiallo et al. (1989). When these cells expressed c-Ha-ras gene, they formed foci on cell culture dish and colonies in suspension. NOG-8 ras cells cultured on cell culture dish expressed syndecan in equal amounts with normal cells in subconfluency state. However, syndecan expression was reduced markedly when these cells showed transformation phenotype, i.e., there was foci on plate or cells grew as colonies in suspension. However, syndecan mRNA levels remained at same level in these different culturing. Thus the regulation of cell surface syndecan is organized post-transcriptionally in these cells. These results indicate that it is a common phenomenon that expression of syndecan is reduced during transformation, but the manner in which it is regulated in different cells could vary from one transformed cell type to another.

Figure 3A:
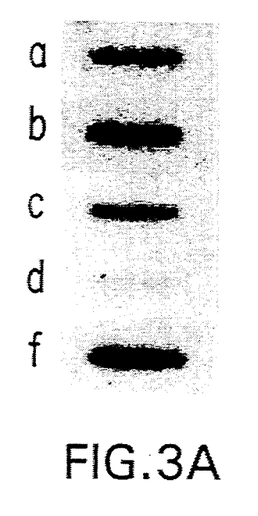
FIGS. 3A is an illustration of a photograph showing suspensions of mouse mammary epithelial cells grown in monolayers with one layer having been transformed by ras-oncogene.
Figure 3B:
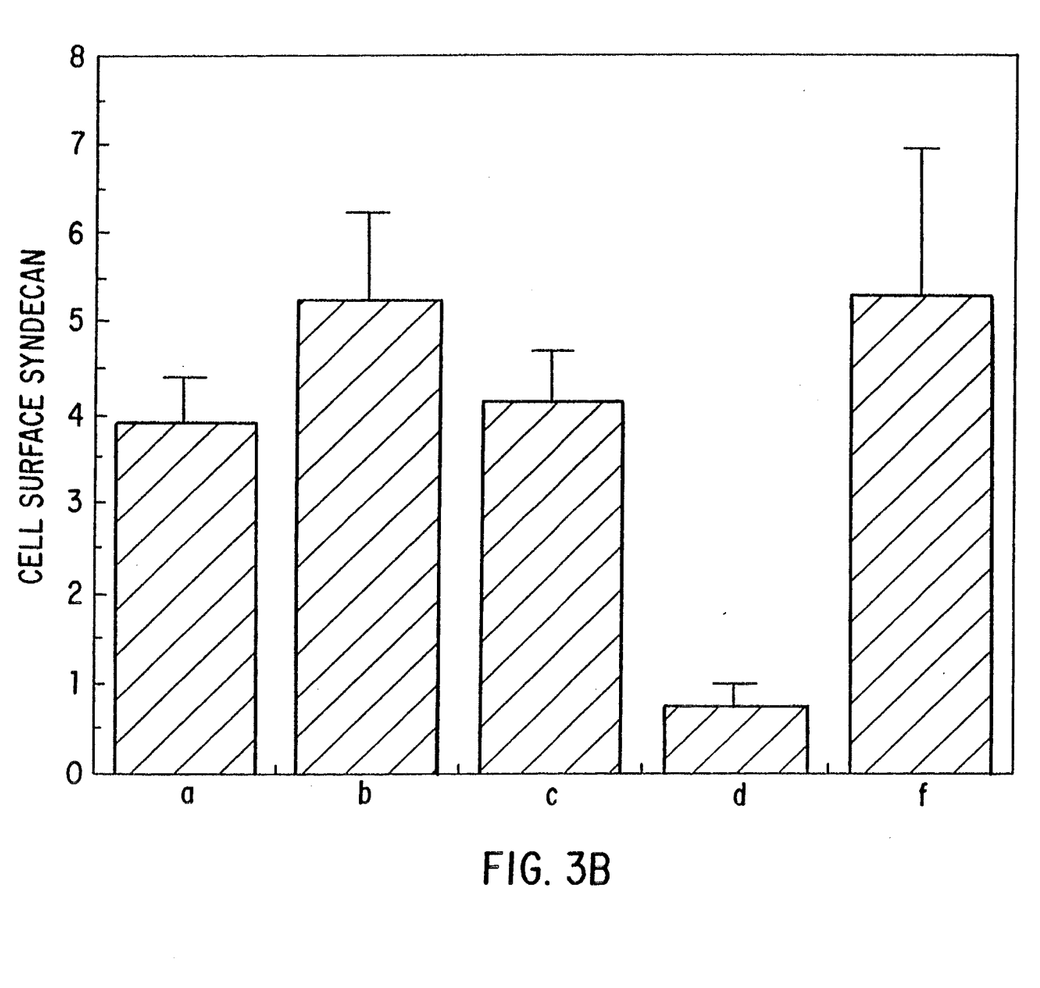
FIG. 3B is a graphical representations of cell surface syndecan content for the monolayers shown in FIG. 3A.

An example of oncogene-induced loss of syndecan expression is shown in FIGS. 3A and 3B.

FIG. 3A is an illustration of a photograph showing suspensions of mouse mammary epithelial cells grown in monolayers with one layer having been transformed by ras-oncogene, and FIG. 3B is a graphical representations of cell surface syndecan content for the monolayers shown in FIG. 3A. Syndecan expression was quantitated in each of the epithelial cells grown in monolayers a, b, c and f and after ras-induction in suspension d. As is apparent, syndecan is lost from the ras-oncogene transformed mouse epithelial cells.

From the above, oncogene-induced malignant transformation also resulted in the loss of syndecan from the surface of epithelial cells indicating that syndecan loss is a common feature of malignant transformation, and that the detection of this loss is a valuable diagnostic tool for the determination of cancer type transformations and their severity.

There are three preferred manners in which to determine syndecan content in accordance with the method of the present invention, that is, biochemical, immunochemical, and molecular biological. The first is based on the biochemical recognition of syndecan, which can be part of the core protein or covalently bound GAG-chains. It has been shown that syndecan can show specific GAG-chains, which can provide specific interactions for syndecan (Elenius et al. (1990) *J. Biol. Chem.* 265:17837–17943; salmivirta et al. (1991) *J. Biol. Chem.* 266: in press). Therefore, syndecan can be detected by providing a syndecan specific ligand. However, other feasible methods utilize syndecan specific antibodies and cDNAs described below.

With the cloning of human syndecan (Mali et al. (1990) *J. Bio. Chem.* 265:6884–6889) or its isolation from human sources, like human mammary cell line HBL-100 (Elenius et al. (1990) *J. Biol. Chem.* 265:17837–17843), it is possible to produce antibodies against human syndecan. This can be accomplished by immunizing animals for polyclonal or monoclonal antibody production, or cells in vitro for monoclonal antibody production with isolated intact human syndecan, its fragments, synthetic peptides or fusion proteins predicted by the human cDNA clone. In the practice of the subject invention, conventional techniques of molecular biology, microbiology, recombinant DNA and immunology may be employed in determining syndecan content and such techniques are explained fully in the literature. See, e.g., *Current Protocols in Immunology* (1990) by Greene Publishing Associates and John Wiley & Sons, Inc.

Using human syndecan specific antibodies, syndecan expression in tissues can be studied with classical immunohistological methods, for example, as is shown in the model illustrated in FIGS. 2A through 2D. In these, the specific recognition is provided by the primary antibody (polyclonal or monoclonal) but the secondary detection system can utilize fluorescent, enzyme or other conjugated secondary antibodies. As a result, a immunohistological staining of tissue section for pathological examination is obtained. Tissues can also be extracted, e.g., with urea and neutral detergent, for the liberation of syndecan for Western-blotting or dot/slot assay (Jalkanen et al. (1985) *J. Cell. Biol.* 101:976–985; Jalkanen et al. (1987) *J. Cell Biol.* 105:3087–3096). In this technique, which is based on the use of cationic solid phases, quantitation of syndecan can be accomplished using isolated syndecan as a standard. This technique can also be applied for body fluids. With these samples, a molar concentration of syndecan will aid to set standard values of syndecan content for different body fluids, like serum, plasma, urine, spinal fluid, etc. The normal appearance of syndecan amounts can then be set by using values from healthy volunteers and comparing these values from values of persons with different diseases or conditions.

Changes in syndecan expression can also be detected by using syndecan cDNA such as human syndecan cDNA. Although syndecan between species is well conserved, the structural differences at the nucleotide level are great enough to prevent the use of mouse syndecan in the detection of human syndecan mRNA. In general, mRNA levels of a given gene product can be detected based on the specific interaction of sense and antisense forms of same nucleotide chains, and in this case those of syndecan. Such can be accomplished by using in situ technique for tissue samples, mRNA protection assay for isolated RNA or primer-directed polymerization of syndecan specific nucleotide chains. All these techniques are fully explained in the literature such as the previously mentioned *Current Protocols in Molecular Biology*.

Specific methods according to the present invention are presented in the following examples. It should be understood that the examples are given for the purposes of illustration and do not limit the invention as has been previously described herein to these particular examples.

EXAMPLE I

Localization of syndecan in transformed epithelial cells. Mouse mammary tumor Shionogi S115 stock cells were routinely cultured in DMEM (Dulbecco's modified Eagle's medium) supplemented with 5% heat-inactivated fetal calf serum (i-FCS), pyruvate (1 mM), glutamine (1 mM), penicillin (100 IU/ml), streptomycin (100 $\mu$g/ml) and testosterone (10 nM). For studies involving hormone treatment, growth medium supplemented with 4% dextran charcoal-treated fetal calf serum (DC-FCS) was used with or without 10 nM testosterone and/or 1 $\mu$M cyproterone acetate. For the experiments, cells were plated at density of 10,000 cells per cm$^2$ on Nunc tissue culture tissue dishes. For cell counting cells were lysed in 10 mM Hepes, 1.5 mM MgCl$_2$ containing Zaboglobin (Coulter Electronics, Ltd.) and the nuclei released were suspended in Isoton (Coulter) and finally counted on a Coulter cell counter.

S115 cells were stained on day four of culture intact as described (Jalkanen et al. (1985) *J. Cell Biol.* 101:976–984). Cell surface proteoglycan, syndecan, was immunolocalized with a rat monoclonal antibody 281-2 against the core protein of the proteoglycan (Jalkanen et al. (1985) *J. Cell Biol.* 101:976–984) and these stainings were controlled using another IgG$_{2a}$ monoclonal antibody Mel-14, specific for lymphocyte homing receptor (Gallatin et al. (1981) *Nature* 304:30–34). Detection of immobilized rat antibodies was done with rabbit anti-rat FITC-conjugate (Janssen Biochimica).

EXAMPLE II

Detection of altered syndecan expression in hormone-induced transformation of epithelial cells. For quantitation of syndecan on cell surfaces of S115 cells, cell monolayers were washed several times with cold PBS and the ectodomain of the molecule was released with bovine pancreatic trypsin (Sigma, Type III; 20 $\mu$g/ml) by 10 min-incubation on ice as described by Rapraeger and Bernfield (1983) *J. Biol. Chem.* 258:3632–3636; (1985) *J. Biol. Chem.* 260:4103–4109. After trypsin inactivation by trypsin inhibitor (100 $\mu$g/ml), cells were centrifuged, supernatant recovered for ectodomain quantitation and cells suspended into Isoton for cell count. Monoclonal antibody 281-2 was radioiodinated by the chloramine-T oxidation method (Stähli et al. (1983) *Meth. Enzymol.* 92:242–253) to a specific activity of $14.1 \times 10^6$ cpm/$\mu$g. For the assay, supernatants from $2 \times 10^5$ cells and a purified control syndecan from NMuMG cells were loaded onto cationic nylon membrane (Zeta-Probe, BioRad) in a mini-fold-slot apparatus (Schleicher & Schuell) as described earlier (Jalkanen et al. (1987) *J. Cell Biol.* 105:3087–3096). Membrane was detached from the slot apparatus and incubated for 1 hour at room temperature in PBS supplemented with 10% FCS to block the membrane. Then it was incubated overnight at +4° C. in PBS containing 125I-labeled 281-2 (10,000 cpm/ml). After washing the filter five times with PBS, it was exposed to Kodak X-Omat film to visualize the bound 281-2. For quantitation each slot was analyzed by LKB Ultroscan XL enhanced laser densitometer and compared to known amount of syndecan from NMuMG cells.

Trypsin-released ectodomains from S115 cells were ethanol precipitated and fractionated on SDS-PAGE gradient (4–10%) gel (O'Farrell (1975) *J. Biol. Chem.* 250:4007-4021). After electrophoresis samples were transformed onto Zeta-Probe membrane using electroblotting 2005 Transphor apparatus (LKB) as described earlier (Jalkanen et al. (1985) *J. Cell Biol.* 101:976–984); Rapraeger et al. (1985) *J. Biol. Chem.* 260:11046–11052) and the membrane was exposed to 125I-labeled 281-2 as described above. Again, isolated syndecan ectodomain from NMuMG cells can be used for comparison.

EXAMPLE III

Detection of altered syndecan gene expression in transformed epithelial cells. Total RNA was isolated using 4M guanidine isothiocyanate and CsCl-pelleting as described by Chirgwin et al. (1979) *Biochem.* 18:5294–5299). RNA aliquots of 15 µg were fractionated on formaldehyde agarose gel (1%) and transferred to Gene Screen Plus membrane. Hybridization with multi-prime (Amersham) labeled insert of PM-4 cDNA probe for syndecan (Saunders et al. (1989) *J. Cell Biol.* 108:1547-1556) was performed under conditions suggested by the manufacturer of the membrane (New England Nuclear). Immobilized probe was visualized by exposing the membrane to Kodak X-Omat film at 70° C. and quantitation of 2.6 kb mRNA was done by densitometric analysis described above. The expression of syndecan mRNA was correlated to ribosomal RNA as described by Denis et al. (1988) *Nucl. Acid Res.* 16:2354–2359. The specificity of syndecan suppression was further studied by probing same samples for rate glyceraldehyde 3-phosphate-dehydrogenase (GAPDH) (Fort et al. (1985) *Nucl. Acid. Res.* 13:1431–1442) and mouse alpha-actin (Minty et al. (1981) *J. Biol. Chem.* 256: 1008–1014).

The cRNA in situ hybridization for paraffin sections was performed according to the method of Wilkinson et al. (1989) *Developm.* 105:131–136. A 535 bp Sac I-Kpn I fragment from the partial cDNA clone for mouse syndecan (PM-4) (Saunders et al. (1989) *J. Cell Biol.* 108:1547–1556) was subcloned (Vainio et al. (1991) *Development,* submitted) into a riboprobe pGEM-4Z vector (Promega, Madison, Wis.). The cloned plasmid containing the insert was linearized with Eco RI or Hind III enzymes and antisense or sense transcripts were produced from complementary strands with T7 or SP6 polymerases in the presence of $^{35}$S-UTP (Amersham, Willshire, UK), respectively. The maximal length of the transcripts was reduced to <200 bp with alkaline hydrolysis and fractions with highest specific activity were collected, precipitated and solubilized in hybridization buffer. Pretreated slides were hybridized overnight at 50° C. and the procedures to remove unspecific binding of the probe (including high stringency washings and ribonuclease A treatment) and autoradiography were done as described before (Wilkinson et al. (1989) *Development* 105:131–136).

EXAMPLE IV

Detection of altered syndecan expression in tissue sections derived from tumors. Tumors were produced in lightly pigmented hairless male mice of the hr/hr C3H/Tif strain (Bomholdgaard, Denmark) by subjecting the animals to UV-A and UV-B irradiation as described by Talve et al. (1990) *Photodermatol. Photoimmunol. Photomed* 7:109–115). During the observation period of 12 months, a total of 83 papillomas, 2 keratoacanthomas, 4 squamocellular carcinomas, one combined carcinosarcoma and 11 sarcomas occurred, with increased tumor formation associating with high UV-A (582 J/cm$^2$) plus high UV-B (erythemally effective=EE) (1.0 J/cm$^2$) plus high UV-B (EE) (0.8 J/cm$^2$) (78 versus 28 tumors). Samples were taken from all grossly observable tumors as well as normal looking UV-exposed skin. A portion of the specimens were fixed in 10% buffered formalin, embedded in paraffin, sectioned and routinely stained with hematoxylin and eosin. The rest of the examples were frozen in nitrogen and sectioned. The lesions were classified according the standard histopathological criteria. Periodic acid-Schiff staining (PAS) was also used in some cases for visualization of the basement membranes as well as Herovic, Weigert's, Masson's trichrom and Gomori's stains for collagen types as well as other stains and electron microscopic analysis when needed.

For immunohistochemical localization of syndecan, a rat monoclonal antibody 281-2 was used. This antibody is specific for the core protein of mouse syndecan ectodomain (18). The avidinbiotin-immunoperoxidase technique was used to detect immobilized 281-2 as described by Hsu et al. (1981) *J. Histochem. Cytochem* 29:577–580). After deparaffinization and rehydration of the tissue sections, the endogenous peroxidase activity was blocked by incubating the slides in 100% methanol containing 3% hydrogen peroxide for 30 min. The sections were then incubated with 2% normal goat serum (Vector Laboratories Inc. Burlingame, Calif.) in Tris buffered saline, pH 7,4 (TBS) for 30 min at room temperature (RT) to minimize non-specific staining. The sections were covered with the primary antibody 281-2 at a protein concentration of 2 µg/ml in 1% (w/v) BSA-TBS and incubated overnight at 4° C. The slides were then incubated with biotinylated goat anti-rat IgG (Jackson's Immunoresearch Laboratories, Inc. West Baltimore, Pa.) at 1:1000 dilution in 1% BSA-TBS for 30 min at RT, and finally with avidinbiotin-peroxidase complex (Vectastain kit, Vector Laboratories, Burlingame, Calif.) for 30 min. at RT. After washes, the peroxidase activity was demonstrated by incubating the slides with 0.5 mg/ml 3,3'-diaminobenzidine tetrahydrochloride (DAB, Polysciences, Inc., Northampton, England) in TBS containing 0.68 mg/ml imidazole and 0.01% hydrogen peroxide for 5 min in the dark. The slides counterstained lightly with Mayer's hematoxylin and mounted Depex Mounting medium (BDH Limited Pool, England). Between all steps, the slides were washed three times with Tris buffered saline (TBS). For control sections, normal rat IgG (Sigma, St. Louis, Mo.) was used at 2 µg/ml. A few frozen sections for each tumor type were also stained, resulting in an identical immunoreactivity as in the paraffin embedded tissue sections. Changes in primary antibody concentration,and incubation times did not alter the staining pattern significantly.

EXAMPLE V

Detection of altered syndecan expression during ras-oncogene-induced transformation. NOG-8 cells present a subclone of normal mouse mammary epithelial cell line, NMuMG and NOG-8 ras cells are a line of NOG-8 cells, which has been transfected with a plasmid containing a glucocorticoid inducible MMTV-LTR promotor linked to a point mutated c-Ha-ras gene. Cells were grown in RPMI-1640 cell culture medium (Gibco) supplemented with 5% dextrancharcoal-treated fetal calf serum (DCC-FCS), glutamine, penicillin (100 IU/ml) and streptomycin (100 μg/ml). In these cells c-Ha-ras gene expression can be maximally induced by adding 1 μM dexamethasone (Sigma) to cell culture medium. DCC-treatment were used to eliminate additional steroids from serum, which might influence the expression of the transfected gene. For suspension cultures bacteriological dishes were covered with 1% agar (Sigma) in RPMI-1640 to prevent possible cell-substrate adhesion. Cells were seeded at a density of $1 \times 10^5$/ml. Cell number was determined after trypsination by using a Coulter Counter (Coulter Electronics, Hialeah, Fla.). PM-4 is a cDNA probe for syndecan originally cloned by Saunders et al (1989) *J. Cell Biol.* 108:1547–1556. It detects two bands of 2.6 kb and 3.4 kb from normal mouse mammary cells.

For RNA preparation, cell culture dishes were washed twice with ice cold phosphate buffered saline (PBS) and then solubilized in 4M GIT buffer (4M guanidine isothiosyanate in 5mM sodium citrate (pH 7.0), 0.1M β-mercaptoethanol and 0.5% N-layrylsarcosine). Total RNA extraction was made by CsCl density centrifugation as described by Chirgwin et al. (1979) *Biochem.* 18:5294–5299. For Northern blot analysis, RNA samples were separated by 1% formaldehyde-agarose gel electrophoresis. These gels were blotted onto GeneScreen hybridization membrane. Filters were prehybridized in 1M NaCl, 1% sodium dodecylsulfate, 10% dextran sulfate, 5×Denhardt's solution, 100 μg/ml salmon-sperm DNA, 50% formamide at 42° C. For hybridization, multiprime-labeled PM-4 or BS-9 probes were added. P32 (Amersham) isotope were used. Filters were washed at 65° C. for PM-4 and at 60° C. for BS-9 in 2×SSC, 1% sodium dodecyl sulfate and autographed on Kodak X-Omat or Fuji X-ray film.

For quantitation of cell surface syndecan expression, cells on culture dish were washed 3 times with ice cold PBS. Then dishes were incubated in 0.5 mM K-EDTA in PBS for 10 min. at +4° C. Trypsin (Sigma, T-8128) was added to final concentration of 20 μg/ml and incubated for 10 mins. at +4° C. Trypsin releases the ectodomain of syndecan into medium (Rapraeger & Bernfield (1985) *J. Biol. Chem.* 260:4103–4109). Then cells were scraped by rubber policeman or colonies suspended and trypsin inhibitor (Sigma, T-9128) was added to final concentration of 100 μg/ml. Cells were centrifuged (5 mins. 100×g), supernatant was collected and cells were counted by a Coulter Counter. Cells in suspension were collected into a tube and colonies were allowed to sedimentate for 5 mins. following removal of supernatant similar to petri dish cultures. Colonies were washed 3 times with ice-cold PBS and treated with trypsin.

The appropriate amount of supernatant which corresponds $2 \times 10^5$ cells was blotted onto cationic nylon membrane (Zeta Probe, Bio-Rad). The membrane was pre-incubated in incubation buffer (10% Fetal Calf Serum, 1 mM Natrium azide, PBS) 1 hr. at room temperature. Radioactively labeled (Chloramine-T method) MnAb 281-2 (Jalkanen et al. (1987) *J. Cell Biol.* 105:3087–3096), which recognizes the ectodomain of syndecan, was added to incubation buffer to final concentration of 10.000 CMP/ml and incubated over night at +4° C. The filter was washed with PBS 10 mins. at room temperature. The washing was repeated 10 times, then the filter was autoradiographed on X-ray film. The autograph was analyzed by GelScan XL ultroscan densitometer (LKB) and GelScan SL 2400 software (LKB), and standardized with isolated ectodomain (Jalkanen et al. (1987) *J. Cell Biol.* 105: 3087–3096).

In summary, the present invention is useful in detecting potentially detrimental transformations by determining syndecan expression and content at, for example, tissue level and in various body fluids. The method may be carried out biochemically, immunohistochemically and molecular biologically using, for example, syndecan specific ligands, antibodies (polyclonal or monoclonal) and cDNA. A special focus of the method is on malignant changes of epithelial cells, which show strong decline in syndecan expression during the process of malignant transformation. The analysis of syndecan expression in hyperplasia is also included, because of its value in the estimation of the seriousness of this premalignant stage. The analyses of syndecan expression is especially useful in the classification of different premalignant proliferative stages of dysplasias.

What is claimed:

1. A method for detecting a malignant or premalignant state of human cells that express syndecan in a non-malignant state, said method comprising:
   a) assaying the amount of syndecan protein or mRNA in said human cells; and
   b) detecting said malignant or premalignant state by detecting an absence of said syndecan protein or mRNA in said human cells.

2. A method for detecting a malignant or premalignant state of human cells that express syndecan in a non-malignant state, said method comprising:
   a) assaying the amount of syndecan protein or mRNA in said human cells;
   b) comparing said amount of syndecan protein or mRNA with the amount of syndecan protein or mRNA in a reference non-malignant sample of the same cell type; and
   c) detecting said malignant or premalignant state by detecting a relative decrease of said syndecan protein or mRNA in said human cells as compared to that in said reference.

3. The method of any one of claims 1 or 2, wherein said human cells are epithelial cells.

4. The method of any one of claims 1 or 2, wherein said human cells are tumor cells.

5. The method of any one of claims 1 or 2, wherein said human cells are plasma cells.

6. The method of claim 5, wherein said plasma cells are obtained from a patient with lymphoma, myeloma or leukemia.

7. The method of any one of claims 1 or 2, wherein said malignant or premalignant state is determined based upon the amount of said syndecan protein.

8. The method of claim 7, wherein the amount of syndecan protein is determined using syndecan specific antibodies.

9. The method of claim 7, wherein the amount of syndecan protein is determined by immunohistological staining.

10. The method of any one of claims 1 or 2, wherein said detection of said malignant or premalignant state is based upon the amount of said syndecan mRNA.

11. A method for detecting a malignant or premalignant change in human cells that express syndecan in a non-malignant state, said method comprising:

a) assaying the amount of syndecan protein in a body fluid; and b) detecting said malignant or premalignant change in said cell by detecting tile appearance of syndecan in said body fluid.

12. A method for detecting a malignant or premalignant change in human cells which express syndecan in a non-malignant state, said method comprising:

a) assaying tile amount of syndecan protein in a body fluid;

b) comparing said amount of syndecan protein with the amount of syndecan protein in a reference sample of the same body fluid from a non-malignant source; and c) detecting said malignant or premalignant change by detecting a relative increase of said syndecan protein in said body fluid as compared to that in said reference.

13. The method of any one of claims 11 or 12, wherein said body fluid is selected from the group consisting of serum, plasma, urine or spinal fluid.

14. The method of claim 13, wherein said fluid is serum or plasma.

15. The method of any one of claims 11 or 12, wherein the amount of syndecan protein is determined using syndecan specific antibodies.

16. The method of any one of claims 11 or 12, wherein the amount of syndecan protein is determined by FACS analysis, Western blotting or dot/slot assay.

* * * * *